US00PP28192P2

(12) United States Plant Patent
Hansen

(10) Patent No.: US PP28,192 P2
(45) Date of Patent: Jul. 11, 2017

(54) ***PANICUM* PLANT NAMED 'BLUE FOUNTAIN'**

(50) Latin Name: ***Panicum virgatum* (L.)**
Varietal Denomination: Blue Fountain

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/999,482

(22) Filed: May 12, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

The new and distinct cultivar of ornamental switch grass named *Panicum virgatum* 'Blue Fountain' with broad blue-green foliage that retains it coloration into the fall. The tall, upright and arching dense culms produce broadly-spreading airy panicles of greenish tan and are retained into winter.

1 Drawing Sheet

Latin botanical classification: *Panicum virgatum* (L.).
Variety denomination: 'Blue Fountain'.

BACKGROUND OF THE PLANT

*Panicum virgatum* 'Blue Fountain', hereinafter also referred by just the cultivar name 'Blue Fountain' and the "new plant" is a new and distinct cultivar of switch grass. The seed was collected by the inventor in the autumn of 2011 as an open pollinated selection from the proprietary hybrid HK10-02 (not patented) at a wholesale perennial nursery in Zeeland, Mich. The individual seedling was initially selected from among many for further observation in the summer and fall of 2012 at which time it was assigned the original breeder code H11-02-03.

The new plant has been successfully asexually propagated by division at the same wholesale perennial plant nursery in Zeeland, Mich. and found to produce stable and identical plants that maintain the unique characteristics of the original plant. The plant is stable and reproduces true-to-type in successive generations of asexual reproduction.

No plants of *Panicum virgatum* 'Blue Fountain' have been sold in this country or anywhere in the world prior to the filing of this application, nor has any disclosure of the new plant been made prior to the filing of this application with the exception of that which was disclosed within one-year period of the filing of this application and was either derived directly or indirectly from the inventor

BRIEF SUMMARY OF THE PLANT

*Panicum virgatum* 'Blue Fountain' differs from its female parent, HK10-02 in that the new plant is taller, has very broad, gray-green foliage and the light, airy, greenish-tan panicles cover the top two-thirds of the plant.

The nearest comparison variety known to the inventors is 'Thundercloud' U.S. Plant Pat. No. 20,665. The new plant is shorter than 'Thundercloud', taller than 'Dallas Blues' U.S. Plant Pat. No. 11,202 and taller and less upright than 'Heavy Metal' (not patented). Other similar switch grass comparison cultivars are succinctly exemplified in Table 1 below including:

TABLE 1

| CULTIVAR | U.S. PLANT PAT. NO. | TOTAL HEIGHT (cm) | INITIAL COLOR |
|---|---|---|---|
| 'Blue Fountain' | current application | 210 | blue green |
| 'Cape Breeze' | U.S. Plant Pat. No. 24,895 | 75 | dark green |
| 'Dallas Blues' | U.S. Plant Pat. No. 11,202 | 193 | grayed blue-green |
| 'Thundercloud' | U.S. Plant Pat. No. 20,665 | 275 | blue green |
| 'Hot Rod' | U.S. Plant Pat. No. 26,074 | 90 | blue green |
| 'Haense Herms' | (not patented) | 100 | green |
| 'Rostrahlbush' | (not patented) | 110 | green |
| 'Shenandoah' | (not patented) | 140 | blue green |

| CULTIVAR | SEASONAL COLOR | SEASON OF CHANGE | HABIT |
|---|---|---|---|
| 'Blue Fountain' | blue green | early July | upright |
| 'Cape Breeze' | purple tipped | late September | compact upright |
| 'Dallas Blues' | purple tipped | late September | upright arching |
| 'Thundercloud' | blue green | none | arching upright |
| 'Hot Rod' | red purple | early spring | upright |
| 'Haense Herms' | red purple | early August | upright |
| 'Rostrahlbush' | red purple | early August | upright |
| 'Shenandoah' | red purple | late July | arching |

The following traits of *Panicum virgatum* 'Blue Fountain', in combination, have been repeatedly observed in multiple generations of asexually propagated plants and distinguish the new plant from all other switch grass plants known to the inventor:

1. Broad blue-green foliage that retains its coloration into the fall.
2. Upright and arching foliage on dense culms producing tall plants.
3. Broadly-spreading airy panicles of greenish-tan that are retained into winter.

BRIEF DESCRIPTION OF THE DRAWINGS

The photographs of the new plant demonstrate the overall appearance of a three-year-old plant growing in an outdoor trial garden in Zeeland, Mich., including the unique traits. The colors are as accurate as reasonably possible with color reproductions. Ambient light spectrum, source and direction may cause the appearance of minor variation in color.

DETAILED BOTANICAL DESCRIPTION

Figure 1:
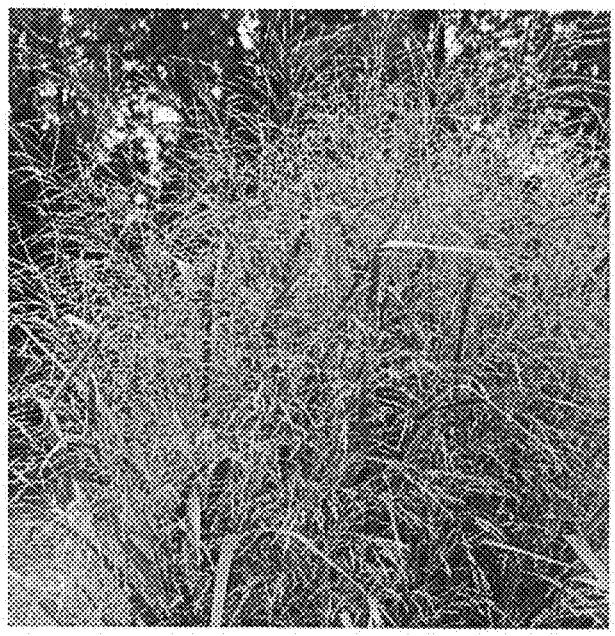
FIG. 1 shows a close-up of the inflorescence in early to mid-August.
Figure 2:
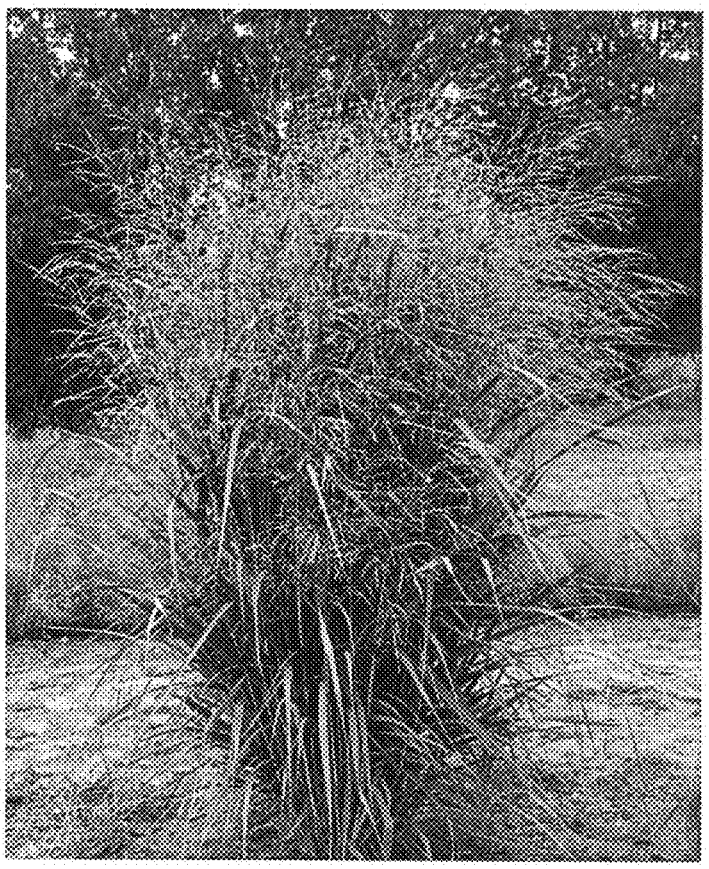
FIG. 2 shows the overall plant in mid-season.

The following descriptions and color references are based on the 2001 edition of The Royal Horticultural Society Colour Chart except where common dictionary terms are used. The new plant, 'Blue Fountain', has not been observed under all possible environments. The phenotype may vary slightly with different environmental conditions, such as temperature, light, fertility, moisture and maturity levels, but without any change in the genotype. The following observations and size descriptions are of a three-year-old plant in a loamy-sand trial garden of a wholesale perennial nursery in Zeeland, Mich., USA in full sun with supplemental water and fertilizer as needed.

Parentage: Female (seed parent) the proprietary hybrid *Panicum virgatum* HK10-02 (female) times open pollinated (male).

Propagation method: By division of the culms.

Time to finishing in a 3.8 liter pot: Rapid; about three months.

Rooting habit: Normal, coarsely branching; root color nearest RHS 155D.

Plant description:

*Plant shape and habit.*—Hardy herbaceous perennial forming tightly rhizomatous clump, with very upright culms topped with finely-textured airy inflorescence producing a narrow clump about 30 percent taller than wide.

*Plant size.*—Foliage height at flowering is about 168.0 cm tall from soil line to the top of the foliage and 210.0 cm tall to top of flowers; about 28 cm wide at soil line and about 150.0 cm at widest point about 125.0 cm above soil.

Foliage description: Glabrous, glaucous; linear; flat; margin with microscopic marginal dentations; sheathed from node of attachment to ligule, adaxial and abaxial surfaces dull; deciduous but persist through winter.

*Foliage size.*—To about 75.0 cm long and about 14.0 mm wide, averaging about 45.0 cm and 12.0 mm wide; shorter at distal end.

*Foliage color.*—Adaxial surface between RHS 133C and RHS N138C; abaxial surface between RHS N138C and RHS 133C; winter adaxial surface between RHS 165C and RHS 164B; winter abaxial surface between RHS 165C and RHS 164B.

*Veins.*—Parallel; midrib about 0.5 mm across; abaxial ridged, adaxial slightly recessed.

*Vein color.*—Adaxial midrib color proximal one-third between RHS 148B and RHS N138D, proximal on-third abaxial midrib nearest RHS N138D, color of distal two-thirds of midrib and secondary veins same as the surrounding leaf on both the top and bottom of the leaf.

*Culm (stem).*—Erect, terete, glabrous, glaucous, dull surface, 75% enclosed by leaf sheath, about seven nodes per culm; about 150 culms per clump.

*Culm dimension.*—To about 175.0 cm long without panicle, average about 165.0 cm; including panicle to about 210.0 cm long with average about 200.0 cm; about 3.5 mm diameter at base; internode length average about 16.5 cm.

*Culm color.*—Between RHS N138C and RHS 133C with portions tinted mixture of between RHS 186C and RHS N187C.

*Node description.*—About 7 per culm, slightly swollen to about 5.0 mm diameter.

*Node color.*—Between blend of RHS N187B and RHS N187C.

Flower description: Finely-branched open panicle, one panicle per culm.

*Flower timing.*—Beginning early August, flowering through late August and panicles dry and remain effective through winter; No fragrance detected.

*Panicle.*—Pyramidal, about 35.0 cm long and 15.0 cm wide; overall effective color between RHS 161B and RHS 160B.

*Rachis.*—Terete, branched, glabrous, glaucous; about 35.0 cm long and about 1.0 mm at base; branches to about 18.0 cm long and about 0.7 mm diameter held at about 60 degree angle above horizontal; color between RHS 137D and RHS N138D.

*Spikelet.*—Usually with two florets; about 15.0 mm long.

*Rachilla.*—Thin, terete, slightly flexuose; between 3.0 mm and 6.0 mm long and less than 0.5 mm diameter; color between RHS 137D and RHS N138D.

*Lower glume.*—About 2.5 mm long and 1 mm wide; without awn; color between RHS 138B and RHS 137D.

*Lemma.*—Upper and lower both about 3.5 mm long and 1.5 mm wide; color between RHS 138B and RHS 137D.

*Gynoecium.*—Two. Stigma: Two, feathered, protruding about 1.5 mm from glume; color between RHS 176B and RHS 177B.

*Androecium.*—Two. Filaments: Fine, hair-like, white, less than 0.1 mm diameter and up to 2.0 mm long. Anthers: Two; dorsifixed, longitudinal; about 2.5 mm long and about 1.0 mm wide; color nearest RHS 22A. Filaments: Fine, hair-like, white, less than 0.1 mm diameter and up to 2.0 mm long. Pollen: Round, abundant; less than 0.1 mm in diameter; nearly transparent, color lighter than RHS 155D.

*Fruit.*—Caryopsis; about 2.5 mm long and about 1.0 mm wide; color between RHS 164D and RHS 161D.

Hardiness, pest and disease resistance: The plant is very drought once established and rust diseases such as *Puccinia* ssp. have not been observed. Hardiness at least from USDA zone 4 through 9. Disease and pest resistance beyond what is typical of that of other switch grasses has not been observed.

I claim:

1. A new and distinct cultivar of ornamental switch grass plant named *Panicum virgatum* 'Blue Fountain' as herein described and illustrated.

* * * * *